(12) United States Patent
Savary et al.

(10) Patent No.: US 7,034,167 B2
(45) Date of Patent: Apr. 25, 2006

(54) PROCESS TO RIBOFURANOSE SUGAR DERIVATIVES AS INTERMEDIATES TO BRANCHED-CHAIN NUCLEOSIDES

(75) Inventors: Kimberly A. Savary, Philadelphia, PA (US); Zhiguo J. Song, Edison, NJ (US); J. Michael Williams, Hillsborough, NJ (US); Feng Xu, Staten Island, NY (US)

(73) Assignee: Merck & Co., Inc., Rahway, NJ (US)

( * ) Notice: Subject to any disclaimer, the term of this patent is extended or adjusted under 35 U.S.C. 154(b) by 219 days.

(21) Appl. No.: 10/729,105

(22) Filed: Dec. 5, 2003

(65) Prior Publication Data

US 2004/0175808 A1    Sep. 9, 2004

Related U.S. Application Data

(60) Provisional application No. 60/431,537, filed on Dec. 6, 2002.

(51) Int. Cl.
*C07D 307/12* (2006.01)

(52) U.S. Cl. .................................... 549/478

(58) Field of Classification Search ................ 549/449, 549/478
See application file for complete search history.

(56) References Cited

U.S. PATENT DOCUMENTS

2004/0158059 A1    8/2004   Tamerlani et al.

FOREIGN PATENT DOCUMENTS

| WO | WO 01/90121  | 11/2001 |
|----|--------------|---------|
| WO | WO 01/92282  | 12/2001 |
| WO | WO 02/32920  | 4/2002  |
| WO | WO 02/057287 | 7/2002  |
| WO | WO 02/057425 | 7/2002  |

OTHER PUBLICATIONS

Y. Murai et al., "A Synthesis and an X-Ray Analysis of 2'-C-, 3'-C- and 5'-C-Methylsangivamycins", Heterocycles, vol. 33, No. 1, pp. 391-404 (1992).

L. N. Beigelman et al., "New Syntheses of 2'-C-Methylnucleosides Starting From D-Glucose and D-Ribose", Carbohydrate Research, vol. 166, pp. 219-232 (1987).

S. Wolfe et al., "A Concise Synthesis of 2'-C-Methylribonucleosides", Tetrahedron Letters, vol. 36, No. 42, pp. 7611-7614 (1995).

R. E. Harry-O'kuru, "A Short Flexible Route toward 2'-C-Branched Ribonucleosides", J. Org. Chem., vol. 62, pp. 1754-1759 (1997).

M. Gallo, "Synthesis of 2'-Modified nucleotides", Molecules, vol. 5, pp. 727-729 (2000).

*Primary Examiner*—Taofiq Solola
(74) *Attorney, Agent, or Firm*—Philippe L. Durette; Melvin Winokur

(57) ABSTRACT

A novel process is provided for the preparation of ribofuranose sugar derivatives which are useful in the synthesis of branched-chain ribonucleoside inhibitors of HCV polymerase for the treatment of HCV infection. Also provided are useful intermediates obtained from the instant process.

13 Claims, No Drawings

PROCESS TO RIBOFURANOSE SUGAR DERIVATIVES AS INTERMEDIATES TO BRANCHED-CHAIN NUCLEOSIDES

CROSS-REFERENCE TO RELATED APPLICATIONS

The present invention is related to U.S. provisional application Ser. No. 60/431,537, filed Dec. 6, 2002, the contents of which are hereby incorporated by reference.

FIELD OF THE INVENTION

The present invention is concerned with a process to novel ribofuranose sugar derivatives which are useful in the synthesis of branched-chain ribonucleoside inhibitors of hepatitis C viral (HCV) polymerase for the treatment of HCV infection.

BACKGROUND OF THE INVENTION

2'-C-Alkylribonucleosides have been described in the patent literature as inhibitors of HCV RNA-dependent RNA polymerase and thereby useful for the treatment of HCV infection. Reference is made to the following publications of international patent applications which disclose branched-chain ribonucleoside inhibitors of HCV polymerase: WO 01/90121 (29 Nov. 2001) and WO 01/92282 (6 Dec. 2001) both assigned to Novirio Pharmaceuticals and Universita degli Studi di Cagliari; WO 02/32920 (25 Apr. 2002) assigned to Pharmasset Limited; WO 02/057287 (25 Jul. 2002) and WO 02/057425 (25 Jul. 2002) both assigned jointly to Merck & Co. and Isis Pharmaceuticals. Synthetic approaches to 2'-C-branched ribonucleosides have previously been described in the chemical and patent literature: U.S. Pat. No. 3,480,613 (25 Nov. 1969); S. R. Jenkins et al. *Carbohydr. Res.*, 166: 219–232 (1987); M. S. Wolfe et al., "A Concise Synthesis of 2'-C-Methylribonucleosides," *Tetrahedron Lett.*, 42: 7611–7614 (1995); R. E. Harry-O'kuru et al., "A Short, Flexible Route Toward 2'-C-branched Ribonucleosides," *J. Org. Chem.*, 62: 1754–1759 (1997); Y. Murai et al., "A Synthesis and X-Ray Analysis of 2'-C-, 3'-C-, and 5'-C-Methylsangivamycins," *Heterocycles*, 33: 391–404 (1992); and M. Gallo et al., "Synthesis of 2'-Modified Nucleotides," *Molecules*, 5: 727–729 (2000). Although the synthetic methods disclosed in these references suffice to prepare small quantities of the desired branched-chain ribonucleosides, they suffer from low and variable yields in the key glycosylation step to elaborate the nucleosidic bond in a stereoselective fashion and therefore are not amenable from an economic perspective to scale-up for the production of kilogram quantities required for preclinical and clinical use.

The present invention provides a novel process to partially protected ribofuranose sugar derivatives from inexpensive starting materials which can be further elaborated into the desired 2'-C-alkylribonucleosides having anti-HCV properties. The instant process makes use of crystalline intermediates to eliminate chromatographic purification steps resulting in considerably improved yields of the final compounds. The invention also provides novel diol intermediates that result from the instant process.

SUMMARY OF THE INVENTION

This invention is concerned with a process for preparing partially protected ribofuranose derivatives of structural formula I:

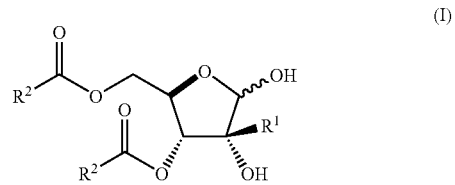

wherein
$R^1$ is $C_{2-4}$ alkenyl, $C_{2-4}$ alkynyl, or $C_{1-6}$ alkyl unsubstituted or substituted with one to three substituents independently selected from fluorine, hydroxy, amino, mercapto, $C_{1-3}$ alkoxy, and $C_{1-3}$ alkylthio; and
$R^2$ is $C_{1-6}$ alkyl or aryl unsubstituted or substituted with one to three substituents independently selected from methoxy, methyl, and fluoro.

DETAILED DESCRIPTION OF THE INVENTION

The process of the present invention involves the preparation of a compound of structural formula I:

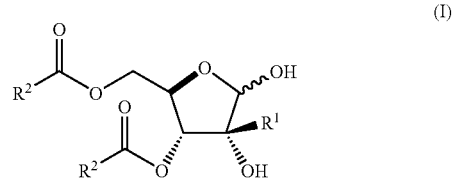

wherein
$R^1$ is $C_{2-4}$ alkenyl, $C_{2-4}$ alkynyl, or $C_{1-6}$ alkyl unsubstituted or substituted with one to three substituents independently selected from fluorine, hydroxy, amino, mercapto, $C_{1-3}$ alkoxy, and $C_{1-3}$ alkylthio; and
$R^2$ is $C_{1-6}$ alkyl or aryl unsubstituted or substituted with one to three substituents independently selected from methoxy, methyl, and fluorine; comprising the steps of:
(a) producing a compound of structural formula II:

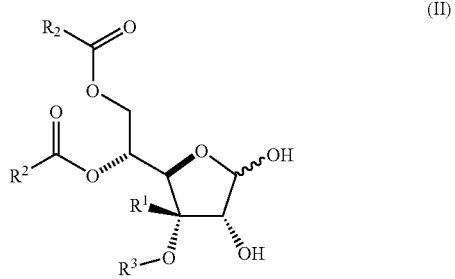

wherein $R^3$ represents benzyl unsubstituted or substituted with one to three substituents independently selected from methyl, methoxy, halogen, and nitro;

by treating a compound of structural formula III:

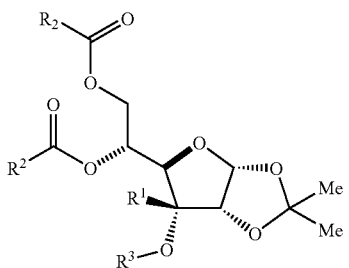

with aqueous acid in an organic solvent;
(b) producing a compound of structural formula IV:

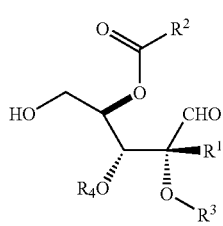

wherein $R^4$ is hydrogen or formyl;
by oxidative cleavage of a compound of structural formula II;
(c) producing a compound of structural formula V:

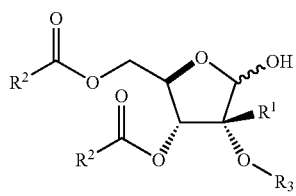

by treating a compound of structural formula IV with base in an organic solvent; and
(d) cleaving the $R^3$ protecting group in a compound of structural formula V.

In one embodiment of the process of the present invention, $R^1$ is methyl. In a class of this embodiment, $R^3$ is benzyl. In a subclass of this class, $R^2$ is phenyl unsubstituted or substituted with one to three substituents independently selected from methoxy, methyl, and fluorine.

In a second embodiment of the process of the present invention, $R^1$ is methyl, $R^3$ is benzyl, and $R^2$ is phenyl unsubstituted or substituted with one to three substituents independently selected from methoxy, methyl, and fluorine. In a class of this embodiment, $R^2$ is 4-methylphenyl (p-toluoyl).

The starting material for the process of the present invention is a compound of structural formula 1-5 in Scheme 1. Compounds of structural formula 1-5 can be prepared from D-glucose via the commercially available 1:2,5:6-di-O-isopropylidene-α-D-ribofuranose ("diacetone glucose") derivative as depicted in Scheme 1 following procedures well-established in the field of carbohydrate chemistry. The initial step entails oxidation of the hydroxyl group in 1-1 to afford ketone 1-2, a known compound. This is followed by addition of a Grignard reagent $R^1MgCl$ or $R^1MgBr$ across the carbonyl double bond in 1-2 to give the tertiary alcohol 1-3. The tertiary alcohol is then protected as its optionally substituted benzyl ether derivative 1-4 by etherification using sodium hydride and an appropriately substituted benzyl chloride or bromide. Subsequently the 5,6-isopropylidene group in 1-4 is regioselectively removed by treatment with aqueous acid. Esterification of 1-5 with an optionally substituted acyl chloride, bromide, or anhydride in the presence of base, such as pyridine or triethylamine, affords the desired intermediate of formula III.

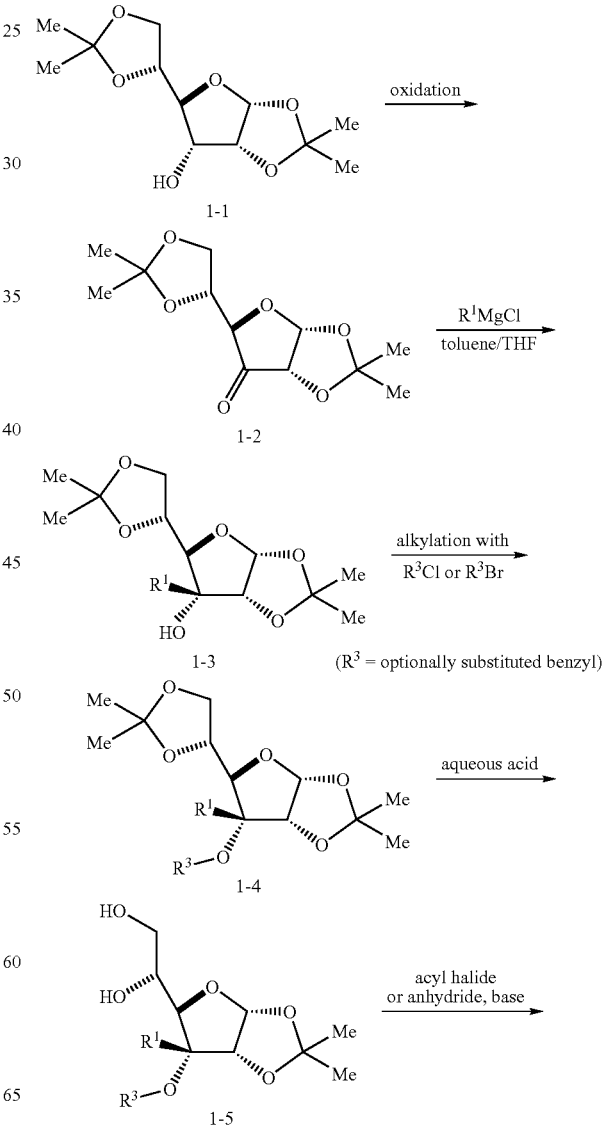

Scheme 1

-continued

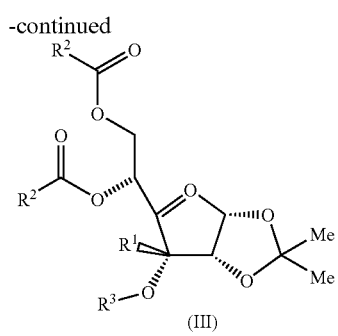

(III)

A synthesis of intermediate 1-5 wherein $R^3$ is benzyl and $R^1$ is methyl has been described by M. Funabashi et al., "Branched-chain Sugars", Carbohydr. Res., 44: 275–283 (1975) and J. S. Brimacombe et al., Carbohydr. Res., 31: 108–113 (1973). A synthesis of the 5,6-di-O-pivaloyl ester derivative of this intermediate has been reported by R. Shiraki et al., J. Org. Chem., 61: 2845–2852 (1996).

The first step in the process of the present invention is hydrolysis of the 1,2-isopropylidene ketal in the intermediate of structural formula III to afford the intermediate of structural formula II. This can be effected by treatment of intermediate III with aqueous acid in a suitable organic solvent. Aqueous acids which can be employed to effect this transformation include aqueous tetrafluoroboric acid; aqueous carboxylic acids, such as aqueous formic, acetic, and trifluoroacetic acid; aqueous alkane- or arylsulfonic acids, such as aqueous methanesulfonic and toluenesulfonic acid; and other aqueous inorganic acids, such as sulfuric, hydrochloric, hydrobromic, phosphoric acid and perchloric acid (HClO4). In one embodiment of this step of the process, the aqueous acid is aqueous tetrafluoroboric acid or aqueous perchloric acid.

The second step in the process of the present invention is oxidative cleavage of the glycol functionality in the intermediate of structural formula II to afford the intermediate of structural formula IV. The reagent of choice for the oxidative cleavage of the glycol is periodic acid or its sodium or potassium salt. Alternatively the glycol cleavage may be accomplished with other reagents such as lead tetraacetate.

The third step in the process of the present invention is cleavage of the formate ester ($R^4$=CHO) in a compound of formula IV which is accompanied by a highly regioselective 1,2 versus 1,3 migration of an ester group and ring closure to afford the hemiacetal intermediate of structural formula V. These transformations are accomplished by treating a compound of formula IV with an organic or inorganic base in a suitable organic solvent, such as methanol, aqueous methanol, tetrahydrofuran (THF), aqueous THF, isopropyl acetate, or mixtures thereof. Organic bases include tertiary amine bases, such as triethylamine, N,N-diisopropylethylamine, N-methylmorpholine, and diazabicyclo[2,2,2]octane; secondary amine bases, such as diisopropylamine; heterocyclic bases, such as pyridine, lutidine, collidine, imidazole, and 4-dimethylaminopyridine (DMAP); amidine bases, such as 1,5-diazabicyclo[4.3.0]non-5-ene and 1,8-diazabicyclo[5.4.0]non-7-ene; and guanidine bases, such as 1,1,3,3-tetramethylguanidine. Inorganic bases include acetate, bicarbonate, phosphate and borate salts, such as sodium acetate and sodium hydrogencarbonate. In one embodiment of this step of the process, the base is diisopropylamine.

The final step in the process is cleavage of the optionally substituted benzyl protecting group in the intermediate of structural formula V. This can be effected by catalytic hydrogenolysis in an organic solvent in the presence of a metal catalyst, such as palladium-on-carbon and $Pd(OH)_2$ on carbon. Suitable organic solvents for the hydrogenolysis step include ester solvents, such as ethyl acetate and isopropyl acetate; hydrocarbon solvents, such as toluene and heptane; ether solvents, such as tetrahydrofuran; and mixtures thereof.

The intermediates need not be isolated but may be processed in situ directly to the final desired compounds of formula I. This eliminates the need for tedious work-ups and purification steps necessarily resulting in yield reductions.

Another aspect of the present invention concerns the following novel compounds of structural formula VI which can be employed as intermediates in the preparation of 2'-Me branched-chain ribonucleosides:

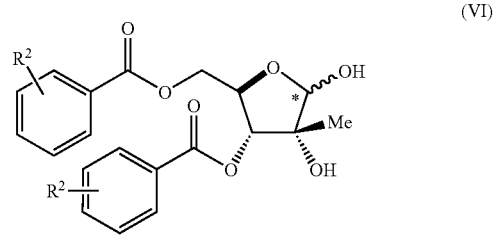

(VI)

wherein $R^2$ is hydrogen, methoxy, methyl, or fluorine.

The "squiggly" bond at the anomeric position indicated with an * in a compound of formula VI is intended to signify undefined stereochemistry at this stereogenic center. Thus, the novel compounds of the present invention are intended to encompass the individual α- and β-anomers as well as all mixtures thereof.

A specific embodiment of this aspect of the present invention is 2-C-methyl-3,5-di-O-(p-toluoyl)-D-ribofuranose of the formula:

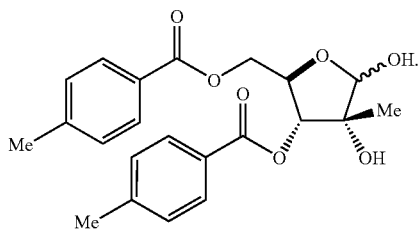

Representative experimental procedures utilizing the novel process of the present invention are detailed below. The following Example is provided for purposes of illustration only and is not intended to limit the process of the present invention to the specific conditions for making the compound.

By halogen is meant fluorine, chlorine, bromine, or iodine.

EXAMPLE 1

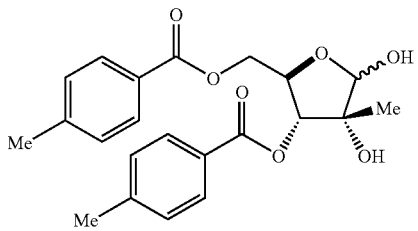

2-C-Methyl-3,5-di-O-(p-toluoyl)-D-ribofuranose

To a solution of 3-O-benzyl-1,2-O-isopropylidene-3-C-methyl-α-D-allofuranose (for preparation, see *Carbohydr. Res.*, 44: 275 (1975) (5.0 kg, 15.4 mol) and pyridine (3.7 kg, 46.2 mol) in 35 L of acetonitrile was added p-toluoyl chloride (5.2 kg, 33.9 mol), and the reaction was heated at 50–55° C. for 12 h. A solution of 6.0 L (46.2 mol) of 48 wt % $HBF_4$ (tetrafluoroboric acid) in 9 L of water was added at 50–55° C. After 2 h, 10 L of acetonitrile was distilled off, and 10 L acetonitrile was added. At 97% conversion, 10 L of acetonitrile was distilled off, and the reaction solution was cooled to 0–5° C. A solution of periodic acid (4.2 kg, 18.5 mol) in 10 L of water was added. After the reaction was aged for 30 min, 35 L of isopropyl acetate and 10 L of water were added. The organic phase was washed with 25 L of water followed by 20 L of aqueous $NaHCO_3$, 15 L of 5% sodium thiosulfate in water, and 15 L of water. The isopropyl acetate solution was concentrated to 10–15 L, and 40 L of methanol was added. The solution was cooled to 0° C. and diisopropylamine (0.78 kg, 7.7 mol) was added. After 2 d at 0° C., aqueous HCl (1N, 7.7 L) was added at 0–5° C. followed by 30 L of isopropyl acetate and 40 L of water. The organic phase was washed with aqueous 1 N HCl, $NaHCO_3$, and brine. The organic phase was dried through azeotropic distillation and treated with activated carbon. The carbon was removed by filtration and the resulting solution was diluted to 75 L with isopropyl acetate and hydrogenated (45 psi, 50° C., 1.5 kg 10% Pd/C) for 24 h. The filtrate was concentrated to 15 L and 60 L of heptane was added at 50° C. The crystalline product was isolated by filtration washing with a 10 L of 20% isopropyl acetate. Drying afforded 4.03 kg of product of the desired diol.

$^1$H NMR ($CDCl_3$, 400 MHz): The ratio of α:β isomers in $CDCl_3$ is about 5 to 1. For the major isomer: δ 7.95–7.90 (m, 4H), 7.26 (d, J=8.0 Hz, 2H), 7.17 (d, J=8.0 Hz, 2H), 5.53 (d, J=7.2 Hz, 1H), 5.22 (d, J=2.8 Hz, 1H), 4.65–4.49 (m, 3H), 3.08 (d, J=3.2 Hz, 1 H), 2.44 (s, 3H), 2.38 (s, 3H), 2.26 (s, 1H), 1.44 (s, 3H) ppm; for the minor isomer: δ 7.95–7.90 (m, 4H), 7.27 (d, J=8.0 Hz, 2H), 7.22 (d, J=8.0 Hz, 2H), 5.16 (d, J=5.6 Hz, 1 H), 5.12 (d, J=5.6 Hz, 1H), 4.66–4.49 (m, 3H), 3.54 (d, J=5.6 Hz, 1H), 2.91 (s, 1H), 2.43 (s, 3H), 1.44 (s, 3 H) ppm.

$^{13}$C NMR ($CDCl_3$, 100 MHz): δ 166.6, 166.3, 165.9, 165.7, 144.6, 144.3, 143.8, 143.7, 129.9, 129.7, 129.3, 129.2, 129.1, 129.0, 127.0, 126.9, 126.4, 126.2, 102.9, 100.8, 79.8, 79.2, 78.7, 76.9, 76.5, 76.4, 65.5, 64.0, 23.5, 21.7, 21.6, and 20.0 ppm.

What is claimed is:

1. A process for preparing a compound of structural formula I:

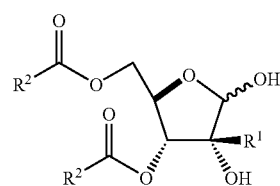

(I)

wherein $R^1$ is $C_{2-4}$ alkenyl, $C_{2-4}$ alkynyl, or $C_{1-6}$ alkyl unsubstituted or substituted with one to three substituents independently selected from fluorine, hydroxy, amino, mercapto, $C_{1-3}$ alkoxy, and $C_{1-3}$ alkylthio; and $R^2$ is $C_{1-6}$ alkyl or aryl unsubstituted or substituted with one to three substituents independently selected from methoxy, methyl, and fluorine;

comprising the step of cleaving the $R^3$ protecting group in a compound of structural formula V:

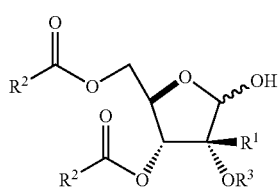

(V)

wherein $R^3$ represents benzyl unsubstituted or substituted with one to three substituents independently selected from methyl, methoxy, halogen, and nitro;

by catalytic hydrogenolysis.

2. The process of claim 1 additionally comprising the step of producing a compound of structural formula V:

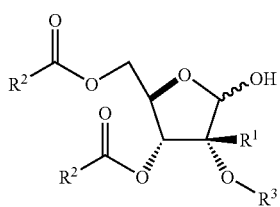

(V)

by treating a compound of structural formula IV:

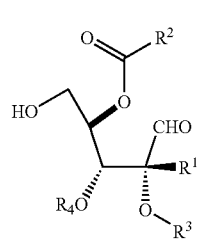
(IV)

wherein $R^4$ is hydrogen or formyl;
with base in an organic solvent.

3. The process of claim 2 additionally comprising the step of producing a compound of structural formula IV:

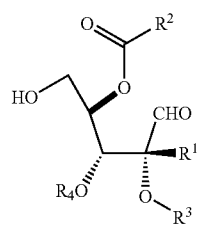
(IV)

by oxidative cleavage of a compound of structural formula II:

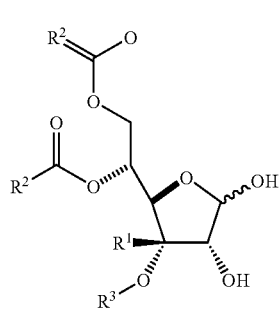
(II)

4. The process of claim 3 additionally comprising the step of producing a compound of structural formula II:

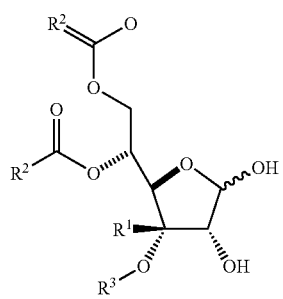
(II)

by treating a compound of structural formula III:

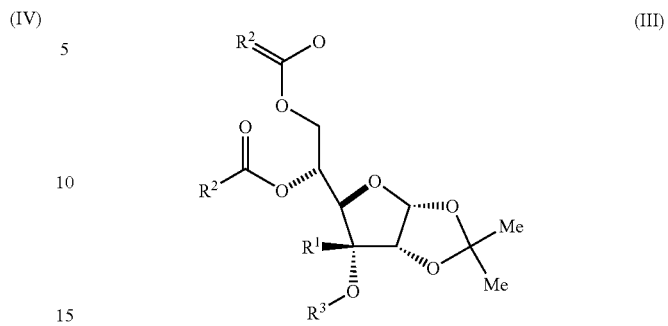
(III)

with aqueous acid in an organic solvent.

5. The process of claim 1 wherein $R^1$ is methyl.
6. The process of claim 5 wherein $R^3$ is benzyl.
7. The process of claim 6 wherein $R^2$ is phenyl unsubstituted or substituted with one to three substituents independently selected from methoxy, methyl, and fluorine.
8. The process of claim 1 wherein $R^1$ is methyl, $R^3$ is benzyl, and $R^2$ is phenyl unsubstituted or substituted with one to three substituents independently selected from methoxy, methyl, and fluorine.
9. The process of claim 8 wherein $R^2$ is 4-methylphenyl.
10. The process of claim 2 wherein said base is diisopropylamine.
11. The process of claim 3 wherein said oxidative cleavage is carried out with periodic acid.
12. The process of claim 4 wherein said aqueous acid is aqueous tetrafluoroboric acid or aqueous perchloric acid.
13. A process for preparing a compound of structural formula I:

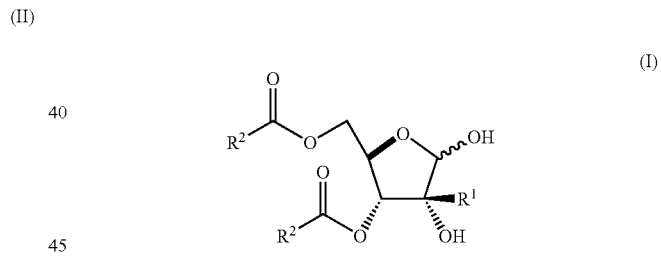
(I)

comprising the steps of:
(a) producing a compound of structural formula II:

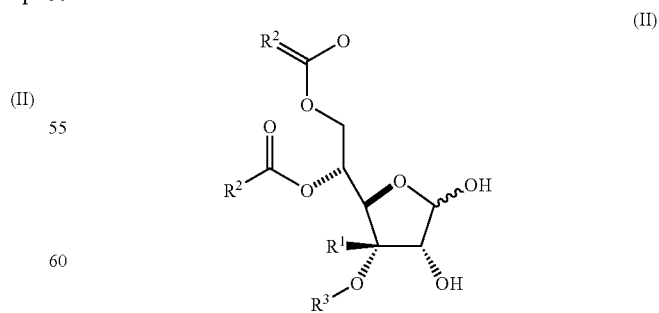
(II)

wherein $R^3$ represents benzyl unsubstituted or substituted with one to three substituents independently selected from methyl, methoxy, halogen, and nitro; by treating a compound of structural formula III:

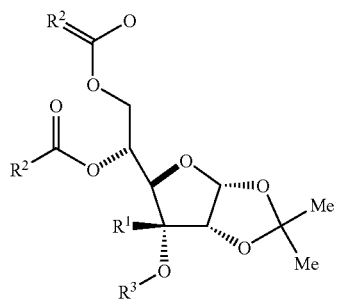

(III)

with aqueous acid in an organic solvent;
(b) producing a compound of structural formula IV:

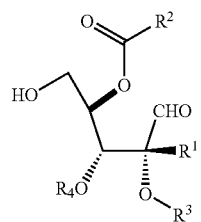

(IV)

wherein $R^4$ is hydrogen or formyl;

by oxidative cleavage of the compound of structural formula II;

(c) producing a compound of structural formula V:

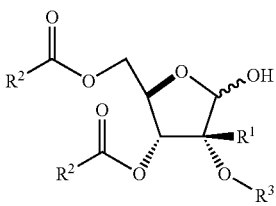

(V)

by treating a compound of structural formula IV with base in an organic solvent; and (d) cleaving the $R^3$ protecting group in a compound of structural formula V by catalytic hydrogenolysis.

* * * * *